United States Patent [19]

Hodosh

[11] 4,191,750

[45] Mar. 4, 1980

[54] METHOD FOR TREATING CANKER SORES

[76] Inventor: Milton Hodosh, 72 Overhill Rd., Providence, R.I. 02906

[21] Appl. No.: 665,161

[22] Filed: Mar. 8, 1976

[51] Int. Cl.² .................. A61K 33/06; A61K 33/00
[52] U.S. Cl. .................... 424/127; 424/154
[58] Field of Search ............... 424/127, 154

[56] References Cited

PUBLICATIONS

Gorgas—Dental Medicine (1884) pp. 261 and 262.
Rusby et al.—The Properties and Uses of Drugs (1930) p. 354.
Dorland—The American Illustrated Medical Dictionary–15th Edit. (1930) p. 1174.

*Primary Examiner*—Sam Rosen
*Attorney, Agent, or Firm*—Salter & Michaelson

[57] ABSTRACT

A compound and method for treating canker sores, the essential ingredient of said compound comprising a nitrate of potassium, lithium, sodium, magnesium, calcium, or strontium, and the method comprising the application of said compound in aqueous solution or nontoxic paste form to the area to be treated.

8 Claims, No Drawings

METHOD FOR TREATING CANKER SORES

BACKGROUND AND SUMMARY OF THE INVENTION

The apthous lesion, or canker sore, as it is commonly known, is a painful oral ulcer which exists in connection with a disease known as apthous stomatitis. The cause of this disease is essentially unknown, and truly effective treatment for curing same and/or relieving the discomfort of same has not been established until conception of the present invention.

Many etiologic factors have been suggested as causing apthous ulcerations. Heredity has been suggested as one; and although there is no evidence of genetic origin in the disease, apthous lesions have been frequently observed in several members of the same family. The disease has sometimes been thought to be viral; and although Herpes simplex ulcers often appear to be similar in appearance to the apthous ulcer, there is no evidence that this virus (Herpes) is the etiologic factor in apthous stomatitis. Tissue cultures have been uniformly negative in identifying Herpes simplex in apthous lesions. Bacterial factors (bacillus crassus) have frequently been thought to be the cause of canker sores; but no one bacterial agent has ever been found to be consistently associated with apthous ulcerations, and there is no evidence of cross-infection. Protoza has sometimes been suggested as a cause of this disease, but no conclusive evidence has ever been established that this is so.

While it is strongly suspected that trauma may contribute to the development of the apthous lesion, it is not considered to be the sole cause. Most likely the tissue was sensitized and made susceptible to the apthous lesion by a traumatic injury. However, it has been observed that a traumatic injury does not result in canker sores in many cases, and particularly in connection with those people not prone to develop such lesions. Another observation is that the eruption of apthous lesions is frequently associated with the onset of menstruation and has also been correlated with post-menopausal women. It has further been observed that recurrent apthae completely subside during pregnancy in otherwise highly susceptible women. Regardless of this apparent hormonal relationship, there is no definite explanation of the mechanism of this phenomenon. Add to this the fact that apthae are frequently seen in men, and the roll of hormones in this disease becomes even more suspect.

There have been numerous reports in the literature of apthous outbreaks following the ingestion of certain drugs or foods. There is, however, little evidence that these eruptions are due to hypersensitive reactions; although some observers feel that hypersensitivity helps to support the reaction. It has also been noted that with apthous ulcers, as with many other kinds of ulcers, acute psychologic factors appear to precipitate attacks of the disease. Although such psychological factors are difficult to analyze, it nevertheless has been popularly concluded that mental stress and psychological disturbances act as a precipitating mechanism to the disease, although they cannot be considered as the actual cause.

Gastrointestinal factors have also been thought to have some relationship to apthous lesions. In a test that was conducted on 120 patients afficted with such lesions, it was found that 41% had dyspepsia, and 9% showed demonstrable peptic ulcerations. It is frequently difficult to separate gastrointestinal disturbance from psychosomatic factors. The gastrointestinal tract is extremely susceptible to emotional disturbances, and lesions of the stomach and lower intestinal tract, coexistent with apthous stomatitis, could be of psychosomatic origin. In fact, the psychosomatic cause of gastric ulcer is well established.

Turning now to the clinical appearance of apthous ulcers, it has been noted that they are single, multiple, round or oval ulcerations. They range in size from 2 to 40 mm. in diameter, and they occur on mucous membrances of the tongue, cheek, lips, soft and hard palates, gingiva, pharynx, and the floor of the mouth. These lesions are also found in the genital, anal, and in conjunctival mucosae. Apthae are extremely painful lesions. They first appear as a small macular red lesion. These areas quickly undergo necrosis, leaving a sharply defined, rounded ulcer, usually varying from 2 to 5 mm. in diameter. The ulceration is fairly deep, with a yellow-white base representing necrotic tissue at the surface. The margins of the ulcer are somewhat indurated, and the marginal mucosa has a surrounding erythamatous zone. The marginal erythema ranges from slight to extensive, depending upon the degree of secondary bacterial involvement. The ulcer is present for approximately seven days, and it undergoes gradual healing. It heals, as a general rule, in approximately ten to fourteen days, and usually leaves no scarring.

Characteristically, there is a recurrent pattern of one or more of these ulcers. The lesions may reoccur as often as one month apart; and there are cases where for a period of years the individual is never without apthous lesions, new ones forming as the previous ones heal. In other cases, apthous attacks may occur two to three times during a year. The lesions often appear following some intense emotional stress, but they may first appear following a gradual change in environment or following an emotional situation, such as the early adjustment period of marriage, boarding school, new employment in a nonfamiliar environment, etc. Apthous sores have been found to occur in cyclic patterns in females. They may appear several days prior to the menstrual period. The first encounter with apthous stomatitis may follow the onset of menstruation. Women susceptible to this lesion often report freedom from the lesions during pregnancy. There is a tendency for a greater frequency of these lesions in females than in males; and although apthae occur at any age level, they seem to occur more often in young adults. The term "periadenitis mucosa necrotica recurrens" is sometimes used to describe large apthae that coalesce to form an elongated, deep ulcerated area.

From a symptomatic standpoint, it has been found that approximately 24 to 48 hours prior to the onset of an apthous lesion there is a vague discomfort, sometimes described as a tingling sensation, in the area. As the tissues undergo necrosis and an ulcer forms, the lesion becomes very painful. The apthous lesions are often considered to be the most painful of oral ulcerative lesions. The discomfort may become particularly intense during periods of fatigue.

Turning to the histopathology of the disease, it has been found that the microscopic picture thereof is nonspecific, generally showing an ulceration of the mucosa. The surface epithelium exhibits a central area of destruction. The connective tissue is densely infiltrated with lymphocytes, polymorphonuclear leukocytes, plasma cells, and histocytes. There is evidence of active fibrosis at the base and sides of the ulcerated area.

Differential diagnosis may include traumatic ulcer, acute herpetic stomatitis, stomatitis medicamentosa, and erythema multiforme. The diagnosis of apthous stomatitis is based upon the clinical manifestations and the patient's history. Biopsis are usually unnecessary and, due to the extreme discomfort involved, are avoided unless necessary to rule out other lesions considered in the differential diagnosis.

Many different substances and agents have heretofore been used in an attempt to cure and/or relieve the discomfort of apthous lesions. For example, cauterizing drugs (escharotic agents), such as phenol, chromic acid, alum and silver nitrate, have been used for many years. These agents alleviate pain by destruction of the small nerve endings. The healing time of the lesion is prolonged due to the escharotic action of these drugs on the surface epithelium and the active fibrosis at the base and sides of the ulcerated areas. Different vitamins have been tried, with inconsistent results; and various antibiotics have also been used, with conflicting results. One observer found that aureomycin applied locally (250 mg. in 10 ml. of water) three times a day appeared to have a definite effect. The duration of the ulcers was reduced from approximately ten to five days, and there was an analgesic effect lasting one-half to two hours. Temporary relief has also been sought, and sometimes achieved, by using milk of magnesia, or various heavy syrups. The transient nature of their benefits renders these preparations impractical. More recently, mucuous membrane adhering compounds ("Orabase", Squibb trademark) have become available to eliminate irritants that delay healing. Other more exotic remedies have been tried with little or no success, such as vaccination with cowpox virus, lactobacillus containing materials, and nutrient supplements.

Corticosteroid agents have also been used in several ways for the treatment of aphtous stomatitis. These agents possess anti-inflammatory properties and have been successful in suppressing or reducing inflammatory processes in the skin and mucous membranes. It has been found that topical applications directly to the apthous lesions avoid the systemic effect of corticosteroid. Topical applications are therefore preferred to the systemic route, especially if long-term treatment is anticipated, since even though some absorption occurs with topical steroids, it is never enough to be of real concern. Topical cortisones used for apthous lesions include hydrocortisone, prednisolone, and dexamethasone. These agents must be frequently and thoroughly applied to the ulcers in ointment or cream form. Corticosteroids, such as triamcinolone, have been incorporated into a base, such as "Orabase", which has the property of adhering to mucous membrane. It is thought, however, that very little, if any, of the active medication is released from the heavy paste so as to be effective.

Attempts have been made to use intralesional injection to treat apthous lesions, this method concentrating the drug at the lesion, while usually avoiding significant systemic effects. The problem with this treatment, however, is that significant discomfort may be present, especially if the apthous lesions are numerous. In addition, patients with gastric ulcers may absorb enough steroid to complicate and aggravate their gastric ulcer.

In situations where patients have numerous lesions and, as a result, topical therapy is unsatisfactory due to the number of ulcers and their inaccessibility, attempts have been made to use systemic treatment. This form of treatment may result in severe complications, particularly with ulcer patients. It should only be used in very severe cases when it is essential that the patient not be incapacitated. Daily dosage of injections of corticosteroids must be gradually reduced. It is hazardous to suddenly stop systemic cortisone administrations, and this treatment should be avoided entirely where gastric ulcers are present.

It will therefore be seen that none of these prior approaches have proven altogether successful in the treatment of canker sores, since none of them quickly cure the condition, and since many of them create other complications.

It is therefore a primary objective of this invention to provide a quick, convenient, safe and relatively painless method of treating apthous lesions, commonly known as canker sores.

Other objects, features and advantages of the invention will become apparent as the description thereof proceeds.

DESCRIPTION OF THE INVENTION

It has now been found that apthous stomatitis can be readily, safely, and effectively treated by the application of an agent or preparation consisting essentially of a nitrate of potassium, lithium, sodium, magnesium, calcium, or strontium. Potassium nitrate has been found to be particularly effective.

In applicant's U.S. Pat. No. 3,863,006, issued Jan. 28, 1975, disclosure is made as to the unusual and surprising effectiveness of potassium nitrate, and, to a lesser extent, lithium nitrate and sodium nitrate, as a desensitizing agent for hypersensitive teeth. It has now been found that potassium nitrate, and, to a lesser extent, the nitrates of lithium, sodium, magnesium, calcium, or strontium, are amazingly effective as a treatment for apthous lesions. These nitrate preparations are safe and easy to administer, and tests have shown, particularly were potassium nitrate is used, that prompt relief of pain is realized within a minute or two following application of the potassium nitrate to the lesions. In some 52 cases where apthous ulcers were present, pain symptoms vanished within one or two minutes following the application of the potassium nitrate preparation. It was equally effective when used in cases with a single or minimal number of lesions and in complex cases where a maximum number of lesions of a recurrent nature were present. In all cases, the severity of the inflammatory reactions was markedly diminished, and healing time was greatly minimized. There was no tissue destruction when the potassium nitrate preparation was applied to the apthae. Most lesions healed in four days or less. The precise physiological action that takes place when the potassium nitrate preparation is applied to the apthae lesion is not known, although it is suspected that the action is directly upon nervous tissue. The potassium nitrate preparation appears to have the special ability to penetrate semi-permeable membranes, rapidly, thus enabling it to quickly relieve pain and enhance healing.

As previously stated, best results have been achieved using a potassium nitrate preparation and, more particularly, a saturated aqueous potassium nitrate solution which is preferably applied to the apthous lesions two to three times a day, such as with a cotton swab or the like. It has been found that pain relief from such a treatment lasts for approximately eight to twelve hours; and hence if the preparation is reapplied two or three times a day, the patient will experience no appreciable discomfort, while the healing process is taking place. Reasonably good results have been achieved using a sodium nitrate solution, although the results are not as effective as those resulting from the use of potassium nitrate. By the same token, some degree of effectiveness has also been achieved using lithium, magnesium, calcium, or strontium nitrate, although these solutions have proven to be somewhat less effective than sodium nitrate, and substantially less effective than potassium nitrate.

The following potassium nitrate formula has been effectively used:
spearmint oil: one drop
saturated potassium nitrate: 20 ml.
glycerol: 5 ml.

In the above formula, the spearmint oil is included for flavoring purposes, i.e., to make the solution more palatable; while the glycerol is added to give the solution more body and make it easier to handle. As previously stated, the solution is applied directly to the apthous lesions by any suitable applicator, such as a cotton swab or the like.

The effectiveness of potassium nitrate in the foregoing treatment has been found to be enhanced by the fact that potassium nitrate is an effective antiseptic and astringent agent.

In addition, potassium nitrate is compatible with many vehicles, i.e., it can be used not only in solution, but it also can be mixed with paste, cream or lotion. It can be mixed with many bases, such as vaseline, methyl cellulose, toothpaste, mouth rinses, and the like; although the aforesaid saturated aqueous solution has proven to be most highly effective. However, some degree of effectiveness has also been achieved where the potassium nitrate is mixed with methyl cellulose to form a nontoxic paste.

It has been found that application of the potassium nitrate preparation to apthous lesions initially causes a momentary stinging sensation. However, within minutes, usually one or two minutes, the treated patients were comfortable and free of pain, able to function normally, including eating. As is well known, the presence of canker sores may be extremely painful during eating to the point where patients severely afflicted have found it difficult to eat normally, if at all.

It will therefore be seen that for the first time a simple, safe and effective remedy for canker sores has been achieved, as a result of the present invention, the scope of which is defined by the appended claims rather than by the description preceding them, and all changes that fall within the metes and bounds of the claims or that form their functional as well as conjointly cooperative equivalents, are therefore intended to be covered by these claims.

What is claimed is:

1. The method of curing canker sores by applying thereto an agent, the essential ingredient of which is an effective amount of a nitrate of one of the following alkali metals: potassium, lithium, sodium, magnesium, calcium or strontium.

2. The method of claim 1 further characterized in that said nitrate is potassium nitrate in an aqueous solution.

3. The method of claim 2 further characterized in that said aqueous solution is a saturated solution of potassium nitrate.

4. The method of claim 2 further characterized in that said aqueous solution also contains a flavoring additive and glycerol.

5. The method of claim 4 further characterized in that said solution comprises approximately four parts saturated potassium nitrate to one part glycerol.

6. The method of claim 1 further characterized in that said nitrate is potassium nitrate mixed with a nontoxic paste.

7. The method of claim 6 further characterized in that said paste consists essentially of methyl cellulose.

8. The method of claim 1 further characterized in that said nitrate is potassium nitrate mixed with a nontoxic ointment.

* * * * *